US006811752B2

(12) United States Patent
Barbera-Guillem

(10) Patent No.: US 6,811,752 B2
(45) Date of Patent: Nov. 2, 2004

(54) DEVICE HAVING MICROCHAMBERS AND MICROFLUIDICS

(75) Inventor: Emilio Barbera-Guillem, Powell, OH (US)

(73) Assignee: BioCrystal, Ltd., Westerville, OH (US)

( * ) Notice: Subject to any disclaimer, the term of this patent is extended or adjusted under 35 U.S.C. 154(b) by 499 days.

(21) Appl. No.: 09/855,920

(22) Filed: May 15, 2001

(65) Prior Publication Data

US 2002/0172621 A1 Nov. 21, 2002

(51) Int. Cl.[7] .......................... B01L 3/02; B01L 11/00; B01L 3/00; C12M 3/00; C12M 1/12

(52) U.S. Cl. ....................... 422/100; 422/101; 422/102; 435/305.1; 435/305.2; 435/305.3; 435/305.4; 435/297.5; 436/180

(58) Field of Search .......................... 422/99, 100, 101, 422/102; 436/180; 435/305.1, 305.2, 305.3, 305.4, 297.5

(56) References Cited

U.S. PATENT DOCUMENTS 4,661,455 A * 4/1987 Hubbard .................... 435/401
5,554,536 A * 9/1996 Rising ...................... 435/305.1
5,587,321 A * 12/1996 Smith et al. ............. 435/305.3
5,597,731 A * 1/1997 Young et al. ............ 435/284.1
5,665,599 A * 9/1997 Minuth .................... 435/288.3
5,688,687 A * 11/1997 Palsson et al. ........... 435/293.2
5,741,463 A * 4/1998 Sanadi ....................... 422/101
5,800,778 A * 9/1998 Chen et al. .................. 422/48
5,800,785 A 9/1998 Bochner
5,858,770 A * 1/1999 Perlman .................. 435/305.3
5,916,812 A * 6/1999 Chen et al. .................. 436/18
5,955,352 A * 9/1999 Inoue et al. ............. 435/287.7
6,037,168 A * 3/2000 Brown .................... 435/288.3
6,086,825 A 7/2000 Sundberg et al.
6,146,883 A * 11/2000 Grass ...................... 435/307.1
6,245,295 B1 * 6/2001 Chen et al. .................. 422/48
6,306,645 B1 * 10/2001 Tanklevsky et al. ..... 435/297.1
6,329,195 B1 * 12/2001 Pfaller ..................... 435/297.2
6,423,536 B1 * 7/2002 Jovanovich et al. ..... 435/287.2
6,555,365 B2 * 4/2003 Barbera-Guillem et al. .......... 435/303.1
2002/0006361 A1 * 1/2002 Sanadi ....................... 422/102
2002/0110900 A1 * 8/2002 Jovanovich et al. ..... 435/286.4
2003/0026738 A1 * 2/2003 Everett ....................... 422/102
2003/0138968 A1 * 7/2003 Fisher et al. ................ 436/180

FOREIGN PATENT DOCUMENTS

WO WO/00/56870 9/2000

* cited by examiner

*Primary Examiner*—Jill Warden
*Assistant Examiner*—Brian R. Gordon
(74) *Attorney, Agent, or Firm*—Benesch, Friedlander, Coplan & Aronoff LLP

(57) ABSTRACT

Provided is a device comprising a plurality of microchambers having a closed vented environment, wherein each microchamber is in operative communication with a filling port and a vent aperture. The device further comprises a base which is sandwiched between two liquid-impermeable membranes, with at least one of the membranes being gas permeable. Also provided is a method for introducing a fluid into a plurality of microchambers of the device, wherein each filling port is aligned with a pipette tip, and the fluid is introduced into and through the filling port. The fluid then flows along a fluid flow groove providing fluid flow communication between the filling port and the microchamber, and into the microchamber.

33 Claims, 5 Drawing Sheets

FIG. 1
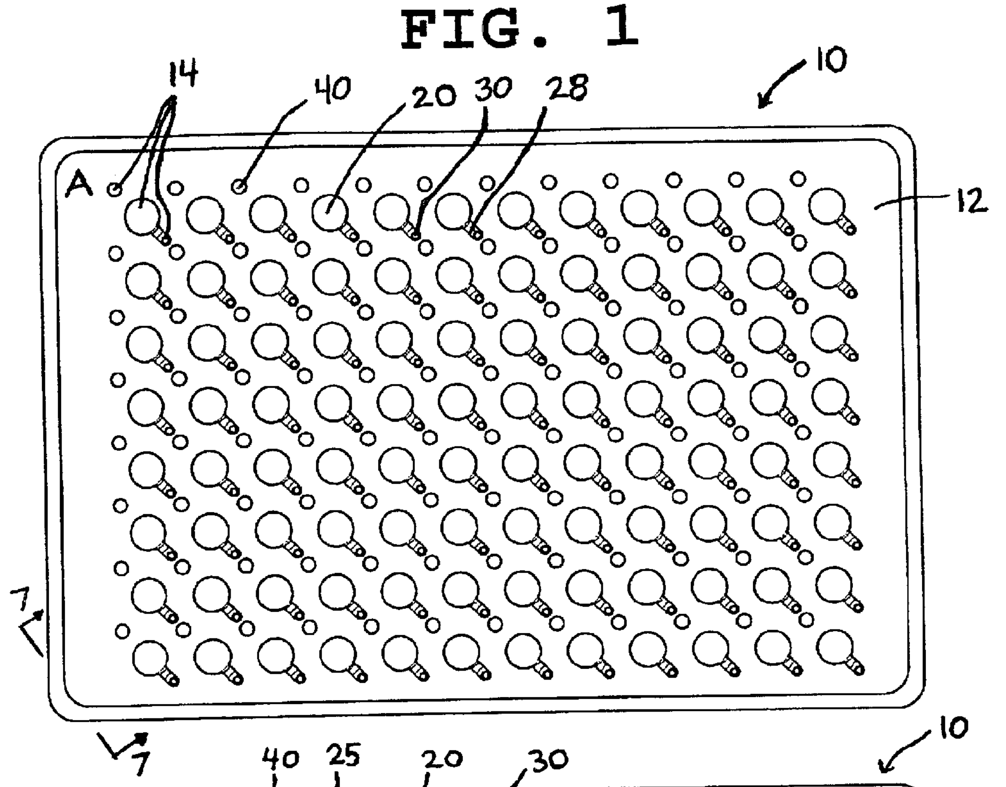
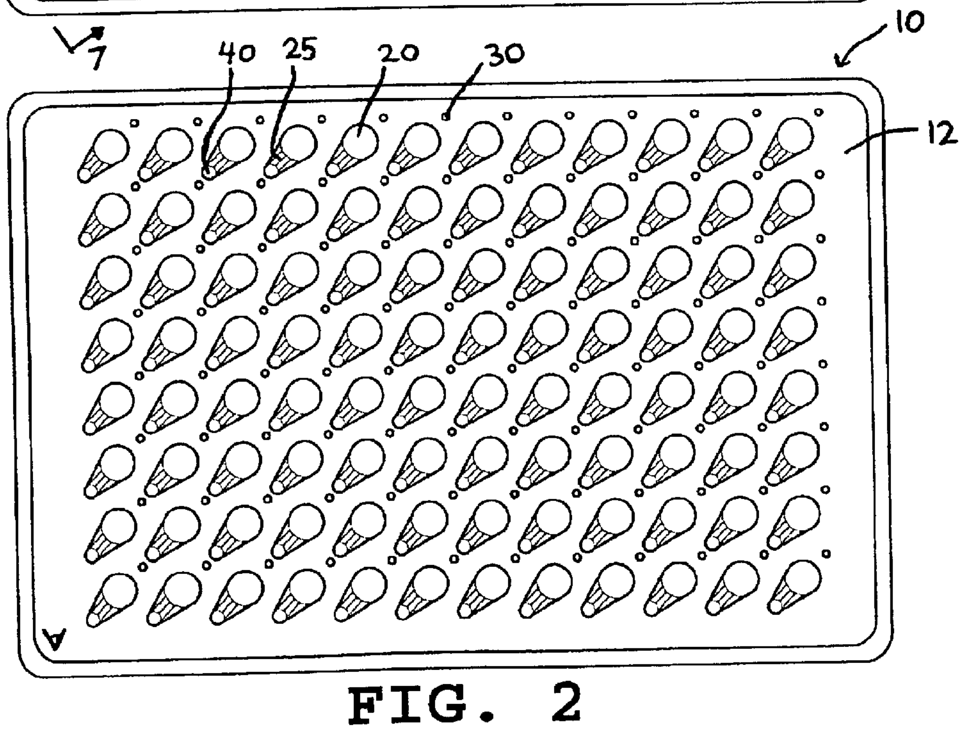
FIG. 2

FIG. 3
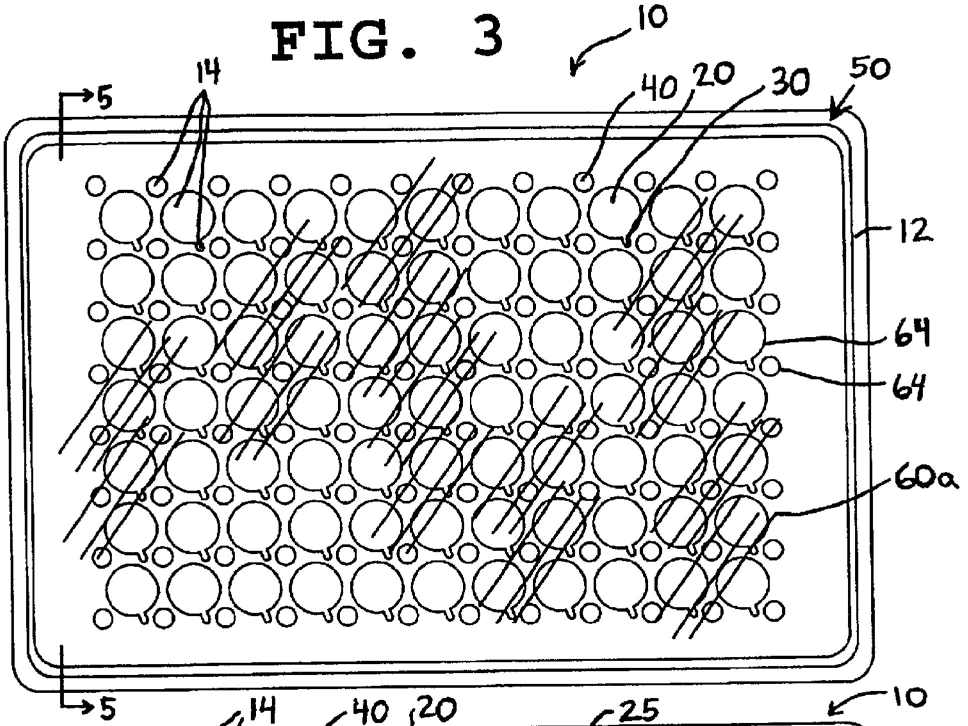
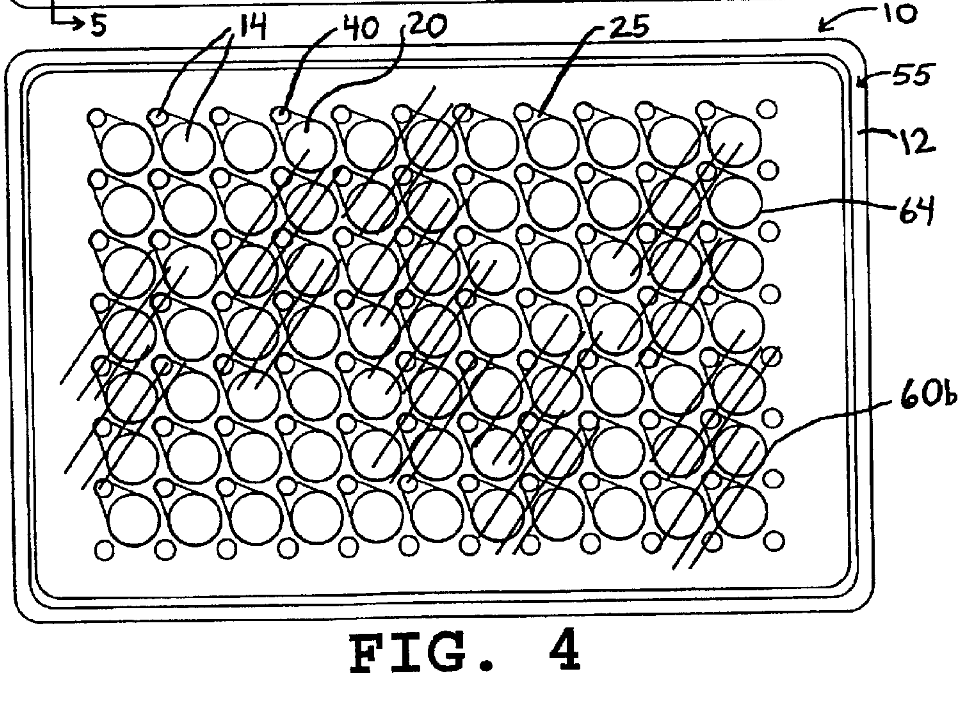
FIG. 4

FIG. 5
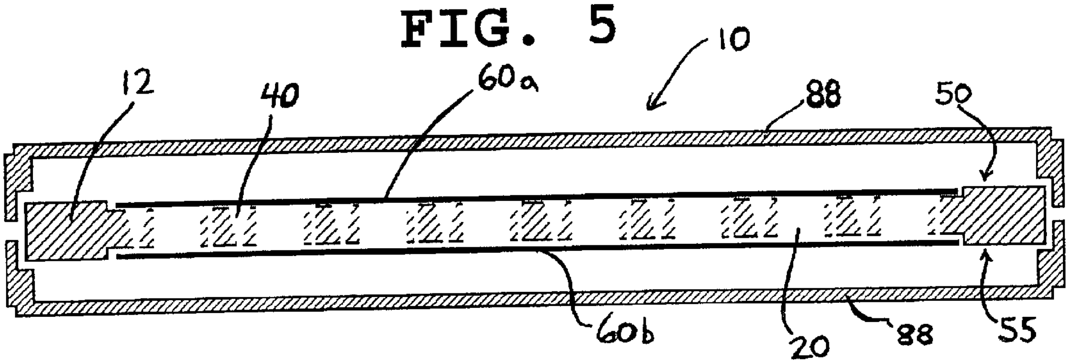
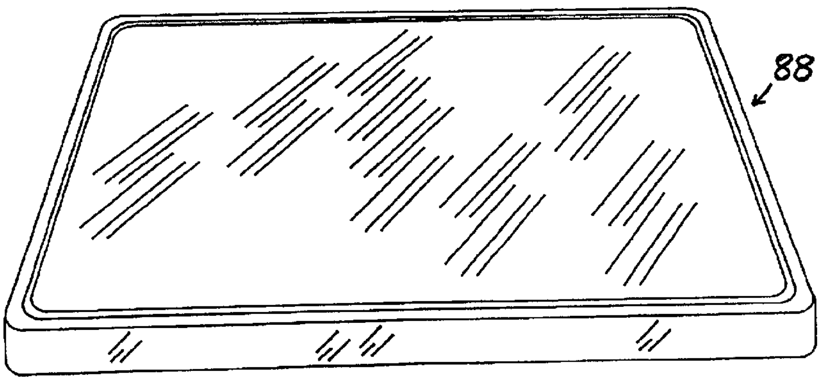
FIG. 6

DEVICE HAVING MICROCHAMBERS AND MICROFLUIDICS

FIELD OF INVENTION

The present invention relates generally to a multichamber device; and more particularly to a device having a plurality of microchambers particularly suitable for biological, biochemical, chemical, genetic, microscopic, or spectroscopic analyses.

BACKGROUND OF THE INVENTION

Genomics, proteomics, and drug discovery are generating a need for expanded versatility of applications for high-throughput screening (e.g., assays performed in large number). Advances in combinatorial chemistry and genomics have resulted in the generation of large libraries of novel compounds. Additionally, combining combinatorial chemistry (novel compounds to be screened) with genomics (expressing potential drug targets in living cells) has put high-throughput screening of live cells in demand. For example, in developing and testing biological substances (e.g., including, but not limited to, genetic vectors, genetic sequences, vaccines, drugs, growth factors, cytokines, chemicals, enzymes, and the like), it may often be desirable to assay for the response of live cells after treatment with a biological substance; and additionally to assay for the responses in high-throughput screening, wherein a cell response may be in a morphological, physiological, biological, or biochemical manner.

The development of automated or semi-automated techniques and instruments currently use microtiter plates with a plurality of wells for assays. However, traditional microtiter plates have several disadvantages. First, in assaying live, adherent cells cultured at the bottom of a well, assay reagents pipetted directly down on the cells may disrupt or otherwise disturb the cells. It is known in the art that some cell monolayers will detach completely from the bottom of a well in response to disruption due to contact with a direct injection of reagent from a pipette. Secondly, since the lid must be removed from a microtiter plate to add reagents, all wells are exposed simultaneously. Reagents pipetted directly down into the exposed wells can splash causing cross-contamination between the exposed wells, as well as causing variance in the reproducibility of results. Additionally, evaporation frequently occurs in conventional microtiter plates leading to variations in fluid volumes between wells. Most of the evaporative loss occurs when removing a microtiter plate from an incubator, and when the lid is removed to add reagents. Also, cultured cells are very dependent upon supplying them with sufficient oxygen for respiration. However, in conventional microtiter plates, the supply of oxygen for cell respiration is from the header space above the cells in each well. Thus, in conventional microtiter plates the volume or surface provided for gas exchange, as relative to the volume or surfaces of the whole container, is either inefficiently used and/or results in limiting the rate of gas exchange or of equilibration of gases. This is even more evident for cells cultured in microtiter wells in which rate of cell growth, cell densities, and total cell numbers, are frequently low due to space, surface area, and gas exchange limitations.

Thus, there is a need for methods and devices capable of performing automated analyses of live cells in high-throughput screening.

SUMMARY OF THE INVENTION

It is a primary object of the present invention to provide a device having one or more microchambers, wherein to introduce a fluid into each microchamber does not require direct access to the microchamber.

It is another object of the present invention to provide a device having one or more microchambers, wherein each microchamber is a closed, vented environment.

It is another object of the present invention to provide a device having one or more microchambers, wherein the device has at least one liquid impermeable, gas permeable membrane in a liquid-tight seal with each microchamber in providing for uniform gas exchange and gas equilibrium available to cells in the microchamber.

It is yet another object of the present invention to provide a device having one or more microchambers, wherein introducing a fluid into each microchamber does not require direct access to the microchamber, wherein each microchamber is a closed, vented environment, and wherein the device has at least one liquid impermeable, gas permeable membrane in a liquid-tight seal with each microchamber in providing for uniform gas exchange and gas equilibrium available to cells in the microchamber, and for preventing the escape of fluid from the microchamber.

It is a further object of the present invention to provide a method for introducing a fluid into the device according to the present invention such as useful in assaying of analyte using the device.

Briefly, the invention provides for a device comprising at least one microchamber, and more preferably a plurality of microchambers. In a preferred embodiment, the device comprises a planar base comprising a plurality of apertures therethrough, wherein the planar base is sandwiched between 2 liquid impermeable membranes, and wherein at least one of the membranes is gas permeable. The membranes are each sealed to the respective surface of the base in a manner that forms a liquid-tight seal around each aperture of the base. Thus, a sheet of membrane is used to individually seal around each aperture, and thereby avoids the need to cut, and the complexity to seal, small membrane pieces and then attach each piece individually for sealing around each aperture. Spatially arranged in the base of the device is one or more sets of apertures, wherein the apertures comprising a set are in operative communication, and wherein a set of apertures comprises: a microchamber with a fluid flow groove; a vent aperture; and a filling port. Preferably, a set of apertures has its own microfluidics in confining a fluid to the set; i.e., each microchamber is in fluid flow communication with its own individual filling port via a fluid flow groove therebetween. To use the device, and for each set of apertures of the base, a fluid is introduced into the filling port. Typically, a pipetting device is used to deliver the fluid, wherein a tip of a pipette is inserted into the filling port, and the fluid is delivered under positive pressure. One or more forces selected from the group consisting of positive pressure associated with pipetting, gravity, capillary force, and a combination thereof, moves the fluid down through the filling port and along fluid flow groove so that the fluid enters into the microchamber in fluid flow communication therewith. As the fluid level rises in the microchamber, air that is in the microchamber (prior to entry by the fluid) is displaced out of the microchamber, through the vent aperture and out one or more vent holes in causing the air to be vented to the exterior of the device. The device may further comprise one or more septums, with a septum being inserted into the desired aperture or apertures of the device. The device may also comprise one or more lids securable to the base of the device, wherein the one or more lids covers a surface of the base selected from the group consisting of a top surface, a bottom surface, and a combination thereof (e.g., a first lid covering the top surface and a second lid covering the bottom surface). Thus, the device according to the present invention provides: (a) a plurality microchambers, each microchamber having a closed, vented environment; (b) at least one gas permeable membrane for a more uniform gas exchange and gas equilibrium, available to cells or other analyte contained within the microchamber, than that provided by the header space in a standard micro-titer plate; and (c) a means by which a fluid may be introduced into a microchamber without requiring direct access to the microchamber (e.g., rather than pipetting a fluid directly into the microchamber and directly onto the analyte, the fluid is dispensed into a filling port and the fluid then flows along a fluid flow groove and into the micro-chamber from the bottom of the microchamber in perfusing (permeating) analyte contained within the chamber comprising the microchamber). Further, provided is a method for introducing a fluid into the device according to the present invention.

The above and other objects, features, and advantages of the present invention will be apparent in the following Detailed Description of the Invention when read in conjunction with the accompanying drawings in which reference numerals denote the same or similar parts throughout the several illustrated views and embodiments.

BRIEF DESCRIPTION OF THE DRAWINGS

FIG. 1 is a planar view of one embodiment of the top surface of the base of the device according to the present invention, wherein corner "A" is provided for purposes of orientation.

FIG. 2 is a planar view of one embodiment of the bottom surface of the base of the device according to the present invention, with corner "A" provided for orientation with FIG. 1.

FIG. 3 is a planar view of another embodiment of the top surface of the device according to the present invention.

FIG. 4 is a planar view of another embodiment of the bottom surface of the device according to the present invention.

FIG. 5 is a cross-sectional view of the embodiment shown in FIG. 3, along lines 5—5, and further shows one or more lids secured to the device.

FIG. 6 is a perspective view of a lid for securing to the device according to the present invention.

DETAILED DESCRIPTION OF THE INVENTION

Definitions

Figure 10:
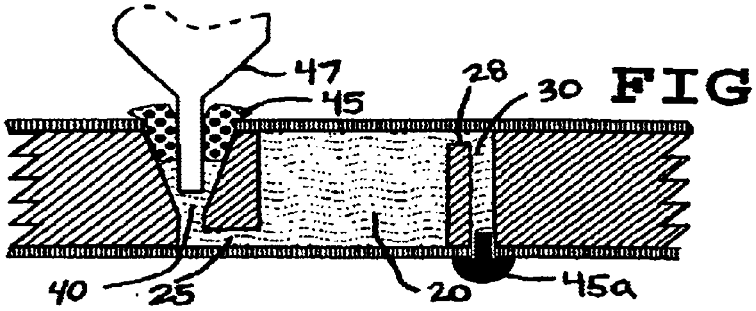
FIG. 10 shows a similar cross-sectional view as in FIG. 7, except that this embodiment further includes one or more septums.

The term "assay" is used herein, for the purposes of the specification and claims, to mean a process for the qualitative detection or for the quantitative or semi-quantitative determination of one or more materials or molecules or substances or cells, ("analyte"), to be tested for.

Throughout the specification of the application, various terms are used such as "top", "bottom", "upward", "downward", "upper", "lower", "first", "second" and the like. These terms are words of convenience in order to distinguish between different elements. While such terms are provided to explain the device relative to positions in which the device may normally be used in an assay, such terms are not intended to be limiting as to how the different elements may be utilized.

The term "gas permeable membrane" is used herein, for the purposes of the specification and claims, to mean a biocompatible material which is liquid impermeable, which permits molecular transfer of gases therethrough (but not of sufficiently large pore size to allow venting of gases therethrough, unless vent holes are added thereto in spatial relation to a vent aperture or venting channel), and which is capable of excluding microbial contamination (e.g., pore size is sufficiently small enough to exclude passage of microbes commonly encountered in contamination of cell cultures), and which has optical transparency and clarity for sufficient for permitting observation which is standard of an assay requiring either microscopic or spectroscopic analysis, as will be described in more detail herein. Thickness of the gas permeable membrane or other membrane used with the device will depend on the desired resultant characteristics which may include, but are not limited to, structural integrity, degree of gas permeability, and rate of molecular transfer of gases. In general, the thickness of a membrane can range from less than about 0.00125 inches to about 0.009 inches. In a preferred embodiment, the thickness of the gas permeable membrane is in the range of about 0.00125 inches to about 0.004 inches. A membrane may typically be comprised of one or more suitable polymers that may include polystyrene, polyethylene, polycarbonate, polyolefin, ethylene vinyl acetate, polypropylene, polysulfone, polytetrafluoroethylene, or a silicone copolymer. As apparent to one skilled in the art, the choice of the composition of the membrane will depend on the desired reagents to be added to the device in using the device in an assay, the type or composition of analyte to be tested for, and the desired degree of gas permeability, rate of molecular transfer of gases, and optical transparency and clarity. In a preferred embodiment, a gas permeable membrane is comprised of polystyrene. In a more preferred embodiment, a gas permeable membrane is comprised of polystyrene which has been treated, on a side of the membrane which may serve as a surface for attachment of anchorage-dependent live cells, by ionization to improve adhesion of the treated membrane surface to anchorage-dependent cells. Ionization of the membrane may render the treated membrane surface more hydrophilic, and can be performed using methods known in the art which include plasma discharge, corona discharge, gas plasma discharge, ion bombardment, ionizing radiation, and high intensity UV light. The term "membrane" is used herein, for the purposes of the specification and claims, to mean an liquid impermeable membrane which is either a gas permeable membrane, or comprises a membrane which is substantially impermeable to molecular transfer of gases (e.g., is incapable of exchanging gas sufficiently to support the growth of cultured cells in the absence of another source for gas exchange); in either case, the membrane is capable of excluding microbial contamination. "Membranes" means a gas permeable membrane used in conjunction with either another gas permeable membrane or a membrane that is substantially gas impermeable (each membrane being secured to their respective surface of the base).

The term "fluid" is used herein, for the purposes of the specification and claims, to mean a liquid or suspension or solution. A fluid may include, but is not limited to, a suspension of cells, a suspension containing analyte, a suspension containing one or more biological substances, a chemical-containing solution, one or more assay reagents, a physiological solution such as a buffer or balanced salt solution, a wash solution, tissue culture medium, cell culture medium, water, and the like.

The term "microfluidics" is used herein, for the purposes of the specification and claims, to generally describe one or more fluid passages, chambers, or conduits which can provide passage of a small fluid volume, preferably a volume in the range of nanoliters (from about 1 to about 1000) to microliters (from about 1 to about 500).

The term "cells" is used herein, for the purposes of the specification and claims, to mean one or more of live cells, fixed cells, cells comprising cellular aggregates, or an organized structure or network of cells in forming a tissue, as apparent to those skilled in the art. Cells typically used in assays are known to those skilled in the art to include, but are not limited to, cell lines, tumor cells, hematopoietic cells, cells isolated from a tissue, genetically engineered cells, animal cells, insect cells, mammalian cells, human cells, transgenic cells, transformed cells, transfected cells, or other cell type desired to be cultured or assayed. Cellular aggregates may be comprised of a single cell type or of multiple cell types. Tissue may be exemplified by, but not limited to, one or more tissue fragments that may be introduced into the device according to the present invention, or systematic introduction of cells of various cell types needed to form a tissue, using standard techniques known in the art (e.g., culturing cells on a three dimensional synthetic (e.g., polyglycolic acid) or natural (e.g., collagen or extracellular) matrix).

In a basic form, the device comprises a base having a plurality of apertures, wherein the base has secured thereto in a liquid-tight sealing, and is sandwiched between, two membranes in forming a plurality of microchambers, wherein at least one of the membranes is gas permeable; microfluidics provided for introducing a fluid into each microchamber of the plurality of microchambers without direct access to the microchambers, wherein the microfluidics comprises a separate filling port which is in fluid flow communication with each microchamber (e.g., each microchamber has its own individual filling port); and a venting system for expelling air out of the device during the introduction of fluid into the microchambers.

As shown in FIGS. 1–5, in a preferred embodiment, device 10 is comprised of planar base 12 having a plurality of apertures. Base 12 may comprise any number of apertures in any arrangement on any multi-well plate format or footprint as known in the art. Thus, the arrangement of apertures depicted in FIGS. 1–4, & 11 represents only illustrative examples, and it is understood that it is possible to arrange the apertures in any other manner with respect to base 12 to achieve its intended purpose, as will be apparent to one skilled in the art. Preferably, device 10 and base 12 are generally rectangular in shape. The dimensions of device 10 and base 12 may depend on one or more factors including, but not limited to, the desired fluid capacity of each microchamber formed therein, and the number of sets of microchambers, vent apertures and filling ports spatially arranged on base 12. In a preferred footprint, base 12 has a length in a range of from about 8 cm to about 13.5 cm, a width in a range of from about 4 cm to about 9.5 cm, and a height in a range of from about 0.1 cm to about 0.8 cm. In a most preferred embodiment, base 12 has a length of about 12.7 cm, a width of about 8.5 cm, and a height of about 0.3 cm. The materials for manufacturing base 12 may be of a basic biocompatible composition that may comprise suitable plastic, thermoplastic, synthetic, or natural materials which can be fabricated into a base structure, thereby achieving the required structural integrity for its intended purpose. Preferably, base 12 is comprised of polymeric material which can facilitate manufacture of the base by molding methods known in the art and developed in the future.

Figure 11:
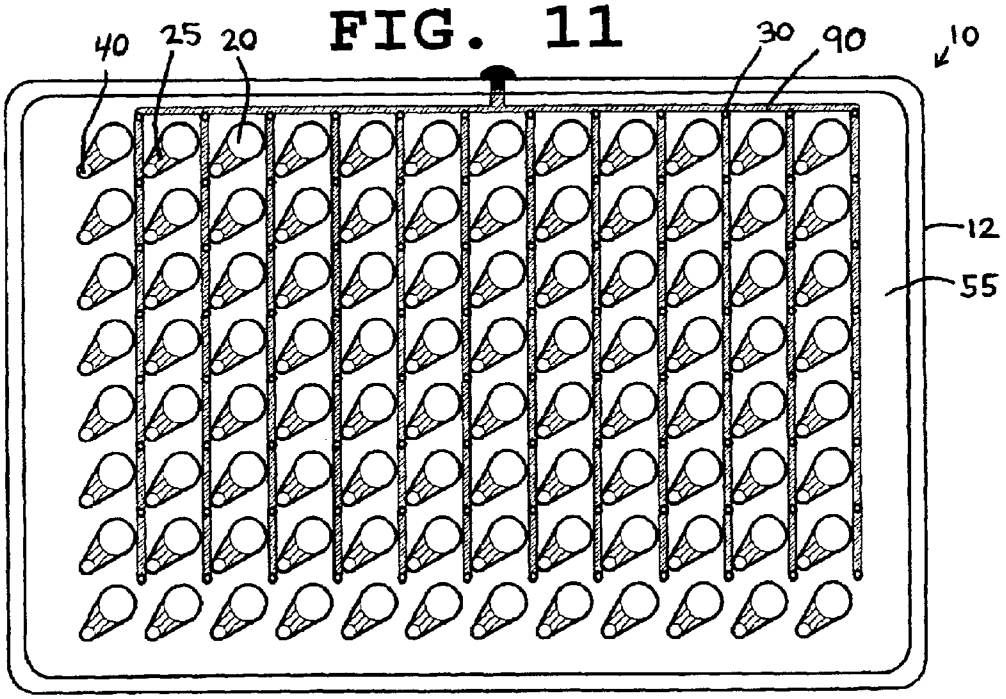
FIG. 11 is a planar view of another embodiment of the bottom surface of the device according to the present invention.

With reference to FIGS. 1–5, illustrated in more detail is the different surfaces of base 12 of device 10. With reference to FIGS. 1 & 3, top surface 50 of base 12 comprises a plurality of sets 14 of apertures, wherein a set 14 comprises microchamber 20, vent aperture 30, and filling port 40. With reference to FIG. 2, in one preferred embodiment, bottom surface 55 of base 12 comprises a plurality of sets 14 of apertures, wherein a set 14 comprises microchamber 20 with fluid flow groove 25, vent aperture 30, and filling port 40. With reference to FIG. 11, and in another preferred embodiment, bottom surface 55 of base 12 comprises a plurality of sets 14 of apertures as illustrated in FIG. 2, and wherein the bottom surface 55 further comprises a venting channel 90 which is connected to each of the plurality of vent apertures 30, in providing a means by which air passing through a plurality of vent apertures may be vented from the device at one location with respect to the device (e.g., one or more vent holes in a portion of the membrane covering the vent channel). With reference to FIG. 4, in another preferred embodiment, bottom surface 55 of base 12 comprises a plurality of sets 14 of apertures, wherein a set 14 comprises microchamber 20 with fluid flow groove 25, and filling port 40. As shown in FIGS. 1–8 & 11, spatially arranged in the base of the device is preferably a plurality of sets of apertures, wherein the apertures comprising a set are in operative communication, and wherein a set of apertures comprises: a microchamber with a fluid flow groove; a vent aperture; and a filling port. A set of apertures has its own microfluidics in confining a fluid to the set; i.e., each microchamber is in fluid flow communication with its own individual filling port via a fluid flow groove therebetween. Such a fluid flow arrangement distinguishes the device according to the present invention from devices which have a single aperture through which a fluid is delivered, and whereby a plurality of channels are used to direct the fluid, from the single aperture, to a plurality of test chambers. The advantage of the device according to the present invention is that by providing a means for separately introducing a fluid into each individual microchamber, a number of different assays can be performed in parallel with the same device (i.e., a different reagent may be added to a microchamber as compared to reagent added to other microchambers in the same device). Thus, for example, in assaying a library of small molecules for inducing a response in living cells (or other analyte), each individual small molecule to be assayed may be separately reacted with living cells (or other analyte) contained in a microchamber, thus being able to assay a plurality of small molecules in parallel in a device comprising a plurality of microchambers.

With reference to FIG. 5, device 10 comprises base 12 having secured thereto two membranes 60, wherein base 12 is sandwiched between membranes 60. Thus, one membrane is secured to a surface of the base which is opposite to the surface to which the other membrane is secured. Membranes 60 are secured to base 12 with a liquid-tight sealing. At least one of membranes 60 is a gas-permeable membrane; and in a more preferred embodiment, both membranes 60 are gas-permeable membranes. Membranes 60 may be secured to base 12 with a liquid-tight sealing using means that may include mechanical means, chemical means, or other suitable means. For example, chemical means, such as the use of an adhesive agent (also encompassing a bonding agent) may be used to secure membranes 60 to base 12 in forming a liquid-tight seal. The adhesive agent may be in the form of a double-faced adhesive tape, a polymeric adhesive, a pressure-sensitive acrylic adhesive, hot-melt adhesive, rubber cement, or any other form of adhesive or bonding agent useful for the purposes attendant to the present invention. Other suitable means may include one or more of thermal bonding, ultrasonic bonding, pressure fit sealing in forming a liquid-tight seal, and a molding process in which the membranes become an integral part of the base.

For example, in a process of assembling the device according to the present invention, each membrane is extended over and applied to its respective surface of the base (see, e.g., FIGS. 2 & 4), and then the membranes are secured to the base with a liquid-tight seal using methods known in the art. In a preferred embodiment of assembling the device, an ultrasonic bonder comprising an ultrasonic horn is used to contact and sonically weld the membranes to the base in securing the membranes to the base with a liquid-tight sealing. In a preferred embodiment of securing each membrane to a respective surface of the device, by securing membrane 60*a* to top surface 50 of base 12, a liquid-tight sealing 64 is formed around each individual filling port 40, and around each individual microchamber 20 (including vent aperture 30). In a preferred embodiment of securing each membrane to a respective surface of the device, by securing membrane 60*b* to bottom surface 55 of base 12, a liquid-tight sealing 64 is formed around each individual vent aperture 30 (if present), and around each individual microchamber 20 (also included within the sealing of microchamber 20 is fluid flow groove 25 and filling port 40). In an embodiment in which the device further comprises a venting channel 90, as illustrated in FIG. 11, a liquid-tight sealing by securing a membrane to the bottom surface of the device also comprises an air-tight sealing formed around the venting channel wherein the venting channel comprises an air-tight passageway, comprising the venting channel and the portion of the membrane covering the venting channel, through which air may flow. As apparent to one skilled in the art, the sealing of a membrane to a surface may comprise melting the membrane to the surface at various points which can be controlled by energy directors on the surface and/or by a neural pattern on the ultrasonic horn used in the ultrasonic bonding process. As known in the art, energy directors are raised ridges or points that are strategically located, for example, to seal an aperture without interfering with other features and aspects of the aperture, in providing a liquid-tight sealing between a membrane and a surface. As known in the art, under pressure and high frequency vibrations (in the process of ultrasonic bonding), typically the energy directors melt in bonding the membrane to the support.

Figure 7:
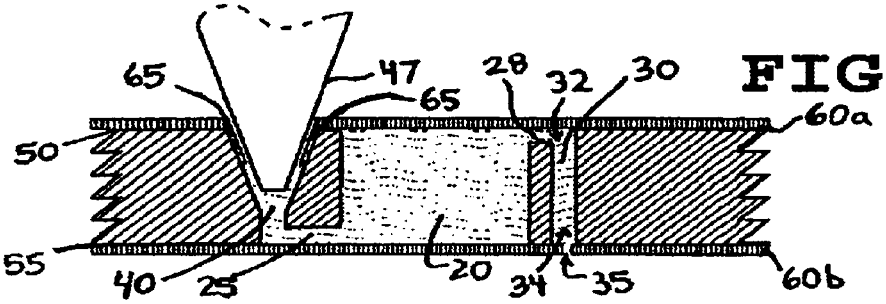
FIG. 7 is a cross-sectional view of the embodiment shown in FIG. 1 along section line 7—7, and further shows a tip and introduction of a fluid.
Figure 8:
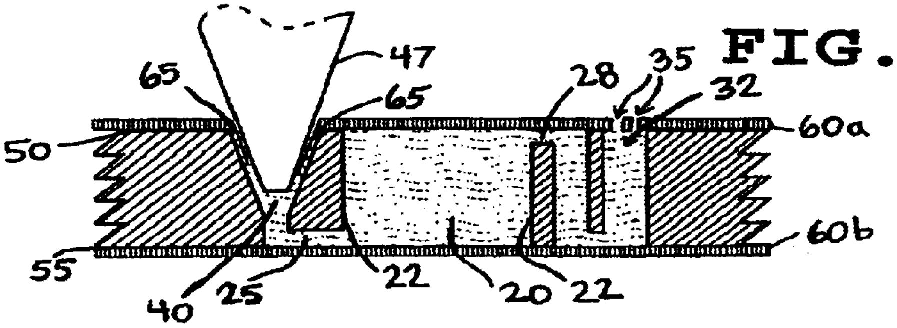
FIG. 8 is a cross-sectional view of a set of apertures through an embodiment shown in FIG. 3.
Figure 9:
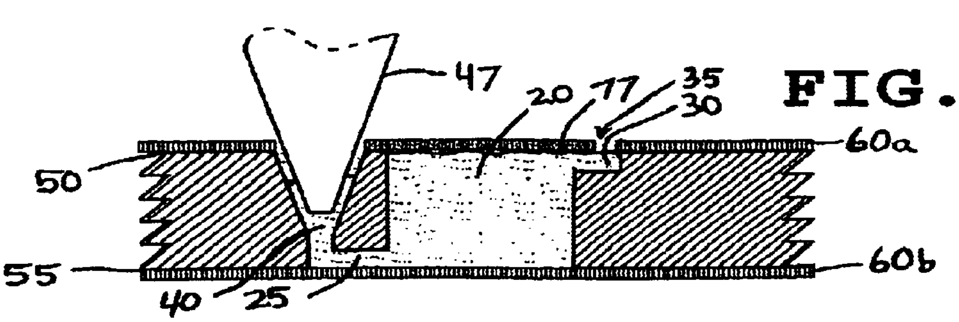
FIG. 9 is a cross-sectional view of a set of apertures through another embodiment as shown in FIG. 3.

Preferably, each filling port 40 comprises a passage that extends through base 12. It will be apparent to one skilled in the art that filling port 40 may define any of a variety of shapes (e.g., cylindrical, and the like) and sizes. In a preferred embodiment, and as illustrated in FIGS. 7–9, filling port 40 is dimensioned to receive a standard tip of a pipette (as typically used for manual and/or automated pipetting). Typically, such shape may include, but is not limited to, a generally conical form. Thus, each of the filling ports 40 may comprise a walled passage, the walls sloping upwardly from the bottom surface 55 of base 12 to top surface 50 of base 12, and outwardly from the center of the passage in forming a passage that comprises a conical shape to receive a standard tip of a pipette. When device 10 comprises a plurality of filling ports, the plurality of filling ports preferably has a spatial arrangement corresponding to that of wells of a microtiter plate or microfluidics device of one of several standard formats known in the art (e.g., 6 well, 12 well, 24 well, 48 well, 96 well, 144 well, 192 well, 384 well, 1536 well, 3456 well, and the like), or other format particularly suited for an automated liquid handling system now known or developed in the future. Thus, preferably the spacing of the filling ports arrayed on the base may correspond to a format of spacing of wells in a microtiter plate or microfluidic apparatus. In a preferred embodiment, the number of filling ports ranges from about 6 filling ports to about 1,600 filling ports.

It will be apparent to one skilled in the art that venting aperture 30 may define any of a variety of shapes (e.g., cylindrical, and the like) and sizes. In one embodiment, as illustrated in FIGS. 7–9, preferably each vent aperture 30 comprises a passage and that extends all the way through base 12 so as to comprise an opening in top surface 50 and, at its opposite end, an opening in bottom surface 55, in allowing airflow through the passage. For example, and as illustrated in FIG. 7, air may be forced out of microchamber 20 into upper opening 32 of vent aperture 30, out through and lower opening 34 of vent aperture 30, and out one or more vent holes 35 formed in membrane 60. In a preferred embodiment wherein the vent aperture has an upper opening and lower opening as illustrated in FIG. 7, the device further comprises a venting channel as illustrated in FIG. 11. Preferably, the venting channel is in operative communication with lower opening 34 of each vent aperture of the plurality of vent apertures. Air displaced from a plurality of microchambers, and through a plurality of vent apertures, flows into venting channel 90 which is in airflow communication with the plurality of vent apertures 30. Thus, venting channel 90 provides airflow communication between a plurality of vent apertures and one or more vent holes in membrane 60. In another preferred embodiment, as illustrated in FIG. 9, vent aperture 30 comprises only a single opening (in extending only partially into base 12), upper opening 32. Air may be displaced out of microchamber 20 into vent aperture 30 and through upper opening 32 of vent aperture 30 in venting the displaced air out (to the exterior) of the device. Each vent aperture 30 may further comprise one or more vent holes 35 which allows passage of air therethrough. One or more vent holes 35 may be formed in membrane 60 covering upper opening 32 or lower opening 34 of the vent aperture; or one or more vent holes may comprise the absence of a membrane over the opening of the vent aperture through which it is desired to vent air. While vent aperture 30 may define any of a variety of shapes and sizes, in a preferred embodiment as illustrated in FIG. 1, vent aperture 30 is generally cylindrically in shape.

While microchamber 20 may define any of a variety of shapes and sizes, in a preferred embodiment as illustrated in FIGS. 1–4, microchamber 20 is generally cylindrically in shape. As apparent to one skilled in the art, the liquid volume capacity of a microchamber may vary depending on its size, shape, the desired liquid volume capacity, and other factors. In a preferred embodiment, the capacity is in an amount in a range of from about 100 nanoliters to about 500 microliters. Preferably, each microchamber 20 comprises a passage that extends all the way through base 12. In a preferred embodiment, as illustrated in FIG. 8, microchamber 20 comprises a chamber defined by: sidewall 22 which generally extends from top surface 50 to bottom surface 55 (e.g., except for areas comprising of the fluid flow groove and microchamber notch) of base 12; that portion of membrane 60*a* which covers microchamber 20 (and, preferably, a liquid-tight seal is formed between the base and membrane around the opening of the microchamber); and a bottom surface comprising that portion of a membrane 60*b* (most preferably a gas-permeable membrane) covering the microchamber, and which is in fluid flow communication with fluid flow groove 25 (and, preferably, a liquid-tight seal is formed between the base and membrane around an area comprising microchamber 20 and fluid flow groove 25; the area may further comprise lower opening 34 of vent aperture 30).

More preferably, as shown in FIGS. 2, 4, & 7–11, microchamber 20 comprises a chamber which, along bottom surface 55 of base 12, communicates with fluid flow groove 25. In that regard, one end of fluid groove 25 communicates with the microchamber 20, and the opposite end of fluid flow groove 25 communicates with filling port 40, in providing fluid flow communication and microfluidics between the filling port and the microchamber, and providing for introducing a fluid into the microchamber without direct access to the microchamber (i.e., without injecting the fluid directly into the microchamber or directly onto analyte that may be contained within the microchamber). The fluid flow groove may also be one of several shapes (e.g., ranging from a narrow channel to a wider channel such as one with a fanned out shape). In a preferred embodiment for when cells or other analyte are attached to a surface defining the microchamber (e.g., the surface being selected from the group consisting of the bottom surface of microchamber 20 as attached on the membrane **60*b*, sidewall 22, and a combination thereof), or attached to a filter inserted into and positioned in the microchamber, fluid flow groove may comprise a fanned out shape (as shown in FIGS. 3 and 4); e.g., the fluid flowing therethrough is less likely to disrupt attached cells or other bound analyte than a more narrow channel. By providing microfluidics and a means for introducing a fluid without directly accessing the microchamber, provided is a fluid flow which causes the fluid to perfuse or permeate the analyte (cells or other analyte) in allowing the fluid to contact analyte in a manner so as to minimize disruption of the analyte. As shown in FIGS. 1, 3, & 8, microchamber 20 may further comprise, in relative proximity to top surface 50 of base 12, a shoulder comprising microchamber notch 28 that provides communication, particularly airflow communication, between microchamber 20 and the adjoining vent aperture 30. Membrane 60*a* and membrane 60*b* form a liquid-tight sealing around the respective openings of the chamber comprising the microchamber, as described previously herein in more detail, in forming a closed environment comprising the microchamber. While the number of microchambers may vary depending on factors which include, but are not limited to, the size of base 12**, the desired number of assays to be performed with the device, the number of filling ports, and the like, in a preferred embodiment the number of microchambers is in a range from about 1 microchamber to about 1,500 microchambers; and in a more preferred embodiment, from about 24 microchambers to about 144 microchambers.

In a device according to the present invention, the filling port, the fluid flow groove, and the membrane which forms a liquid-tight sealing around an area comprising the fluid flow groove and the microchamber in forming the bottom surface of the microchamber, comprise microfluidics that provide for introducing a fluid into a microchamber without directly accessing the microchamber. Microchamber 20, vent aperture 30, and one or more vent holes 35 (aligned with the vent aperture, and formed in the portion of the membrane covering the vent aperture in forming a liquid-tight sealing with the base) provide a venting system for expelling air out of the device during the introduction of fluid into the microchambers. The venting system may further comprise a venting channel as previously described herein in more detail. A closed environment is provided for each microchamber by a membrane covering each opening of the microchamber, wherein the closed environment is formed by a liquid-tight sealing comprising a membrane secured around the microchamber and secured to the top surface of the base, and the liquid tight sealing comprising a membrane secured around the microchamber and secured to the bottom surface of the base. Thus, combining the venting system with the closed environment, each microchamber comprises a closed, vented environment.

In a further embodiment, one or more apertures may further comprise a septum, inserted therein, which may further contribute to a closed environment (thus, the device according to the present invention may further comprise a plurality of septums). The septum may comprise a slitted septum (slitted to facilitate tip insertion), a plug to seal off the end of the aperture into which it is inserted (e.g., to further prevent microbial contamination), or a septum which has one or more vent holes. For example, as illustrated in FIG. 10 each filling port 40 may further comprise a septum 45 which may further contribute to a closed environment. A septum generally comprises an elastomeric material which is inserted into an aperture. In the case of a septum for use with a filling port, it is preferable that the septum can provide a closure which is puncturable (e.g., by a pipette tip), and which is capable of resealing in a leak-proof manner even after multiple punctures. Thus, for example, with reference to FIG. 10, filling port 40 may further comprise septum 45 which is inserted and extends into filling port 40. Septum 45 should permit the introduction of pipette tip 47 through septum 45 and into filling port 40, seal tightly around tip 47 to prevent leakage through septum 45 while tip 47 is present in septum 45, allow withdrawal of tip 47 without unduly restricting the passage of tip 47 through septum 45, and allow for resealing of septum 45 in maintaining a closed environment. Also illustrated in FIG. 10 is use of a septum **45*a* to plug venting aperture 30** (e.g., after the components have been added to the filling port, and after the microchamber has been vented) As an example, plugging the venting aperture may be preferable such as when a fluid has already been introduced into the microchamber and an assay is performed over an extended period of time (e.g., ranging from several hours to days).

The septum may be comprised of a suitable elastomeric material, and may further comprise one or more additives such as a colorant, filler, and the like. The elastomeric material may be natural or synthetic. The elastomeric material may be a material including, but not limited to, silicone rubber, fluorocarbon rubber, butyl rubber, polychloroprene rubber, a silicone elastomer composite material, thermoplastic elastomer, medical grades of silicone rubber, polyisoprene, a synthetic isoprene, and a combination thereof. In a preferred embodiment, the elastomeric material is substantially nontoxic to cultured cells (e.g., mammalian cells of a cell culture). Additionally, it is preferred that the elastomeric material is compatible with sterilization processes such as gamma irradiation. Preferably, the elastomeric material composition and durometer provide a combination that provides superior resealing qualities, particularly when utilized in conjunction with a standard pipette tip in an automated liquid handling system known in the art, as well as certified as nontoxic to cultured cells, as determined by standard assays known in the art. The septum may be manufactured using methods known in the art, such as by a molding process. The precise dimensions of the septum may be varied depending on factors such as the depth and size of the aperture into which it is to be inserted, and the forces needed to maintain the septum in position in the aperture into which it is inserted. In a preferred embodiment a septum for use with a filling port is pre-slit to facilitate introduction of a tip therein. In one embodiment, membrane 60 overlays septum 45 (e.g., a membrane 60 is placed over the septa and base, and then the membrane is secured to the base; and in an alternate embodiment, membrane 60 seals around, but does not overlay, septum 45 (e.g., a membrane is secured to the base, an opening is created over the aperture, and the septum is then inserted into the aperture).

Figure 12:
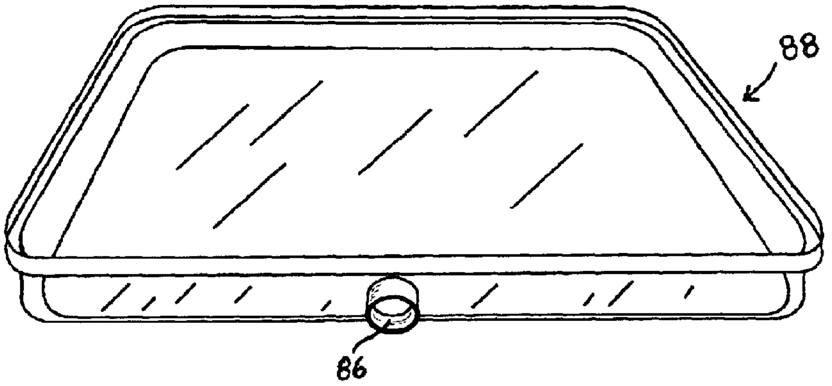
FIG. 12 is a perspective view of another embodiment of a lid for securing to the device according to the present invention.

In a further embodiment of providing a closed, vented environment, and as illustrated in FIGS. 5 & 6, device 10 according to the present invention may further comprise one or more lids 88. A lid may be comprised of a suitable polymeric material or other material providing the structural rigidity for its intended function. The lid itself will typically be comprised of a liquid impermeable material, and more preferably may be comprised of a liquid impermeable, gas permeable material. Also it is preferable for the one or more lids to be comprised of a material that is transparent (e.g., a clear plastic, or the like), so as to facilitate viewing of the device and its contents when the device further comprises the one or more lids detachably secured thereto. A lid is dimensioned to securely fit to device 10. While a fiction fit is the preferable means by which the one or more lids detachably secures to the device, other standard means in the art may be used for detachably securing the one or more lids to the device (e.g., snap-fit, non-permanent adhesive, and the like). The device may further comprise one or more lids selected from the group consisting of a lid detachably secured to the top surface of the device, a lid detachably secured to the bottom surface of the device, and a combination thereof (e.g., a first lid detachably secured to the top surface of the device and a second lid detachably secured to the bottom surface of the device). The one or more lids may be useful in several applications apparent to those skilled in the art. For example, the one or more lids may be used to protect the device before use (e.g., prevent dust or other contaminants from accumulating on the membrane surface (s) of the device, and/or to prevent scratching of the membrane surface(s)), and removed just prior to using the device in an assay. Alternatively, after initiating the assay process using the device, the one or more lids may be detachably secured to the device in further providing a closed and vented environment during the assay process (e.g., incubation or assay time in which a desired period of time expires since assay initiation, at which expiration time the assay is then further manipulated (e.g., the assay results are determined)). In another embodiment, the one or more lids comprises a lid detachably secured to the bottom surface of the device, wherein lid 88 further comprises a vacuum port 86, as illustrated in FIG. 12. Vacuum port 86 comprises a passageway which may be hooked up (e.g., operatively connected) to a vacuum source (e.g., mechanical pump, or air compressor, or other vacuum pump means known in the art) or suction lines (not shown) by tubing or other connection means known in the art. Accordingly, in one embodiment the device according to the present invention may further comprise a lid detachably secured to the bottom surface of the device, wherein the lid further comprises a vacuum port.

After introduction of fluid into a device, the lid further comprising a vacuum port provides a method to remove the fluid. Thus, provided is a method for removing fluid from the device, wherein the device further comprise a lid detachably secured to the bottom surface of the device, and wherein the lid further comprises a vacuum port, the method comprising hooking up the vacuum port to a vacuum source; and applying a vacuum to the device, wherein the vacuum draws fluid contained within the device to flow through the venting system of the device and through the vacuum port so as to be removed from the device. In that regard, the vacuum may cause the fluid to flow through the venting system comprising vent apertures and one or more vent holes aligned therewith. Alternatively, where the venting system of the device further comprises a venting channel, the fluid may flow through the respective vent apertures, into the venting channel, and out one or more vent holes positioned to allow venting from the venting channel. This method for removing a fluid from the device may be desirable during an assay using the device, such as to remove fluid contained within the device before a subsequent addition of fluid to the device is introduced through the plurality of filling ports. For example, as apparent to one skilled in the art, washing steps are performed to rinse out a first reagent from the assay system before a second reagent is added.

In providing a closed, vented environment, each individual microchamber is in fluid communication, via fluid flow groove, with a filling port; and is in airflow communication with a vent aperture. Thus, spatially arranged adjacent to, and in operative communication with, a microchamber is a vent aperture and filling port. As illustrated in FIG. 9, this arrangement and operative communication enables a fluid 77, introduced into (e.g., dispensed into, expelled into, or the like) and through filling port 40, wherein fluid 77 exits filling port 40 and flows along and between fluid flow groove 25 and a portion of membrane **60*b* secured to bottom surface 55 of base 12 which is parallel to and covers fluid flow groove 25. Fluid 77 flows along and between the fluid flow groove and membrane, and reaches and enters an opening of microchamber 20 which is in fluid flow communication with the fluid flow groove, wherein the level of fluid 77 then rises up into microchamber 20. Vent aperture 30 is spatially aligned, and in airflow communication, with microchamber 20. As fluid 77 enters into and rises in microchamber 20, the relative force of fluid 77 displaces air, that is residing in microchamber 20, upward toward membrane 60*a* covering microchamber 20. In a preferred embodiment, the displaced air flows along microchamber 20 and into vent aperture 30, in communication with microchamber 20, so that the displaced air is then forced through one or more vent holes 35 (in air flow communication with the vent aperture or in air flow communication with the venting channel) in exiting device 10. In a more preferred embodiment, the air is displaced out of microchamber 20 and flows along microchamber notch 28 (that provides communication between microchamber 20 and vent aperture 30) and into vent aperture 30, and then the air is forced through vent aperture 30 and into and through one or more vent holes 35 (in air flow communication with the vent aperture) in exiting device 10. As illustrated in FIG. 7, the one or more vent holes 35 are formed in membrane 60*b* which covers lower opening 34 of vent aperture 30, wherein the membrane is secured to bottom surface 55 of base 12 of device 10. In another embodiment, the one or more vent holes are formed in membrane 60*b* which covers an opening of venting channel, wherein the membrane is secured to bottom surface 55 of base 12 of device 10. Alternatively, and as illustrated in FIGS. 8 and 9, one or more vent holes 35 are formed in membrane 60*a* which covering upper opening 32 of vent aperture 30, wherein the membrane is secured to top surface 50 of base 12**. To alleviate air pressurization in the microchamber caused by the fluid entering into and rising in the microchamber, it is desirable to force the air, displaced from the microchamber, through the vent aperture and through the one or more vent holes so that the air exits out of the device. The venting system may further comprise a venting channel providing airflow communication between each vent aperture (of the plurality of vent apertures) and the one or more vent holes. Preferably, the venting system serves to quickly evacuate the air that is forced into and through the vent aperture. As apparent to one skilled in the art, the one or more vent holes may be formed in a membrane by any one of several methods known in the art, which may include, but are not limited to, mechanical means for punching one or more holes, or formation of one or more during the production of the membrane. The one or more vent holes are sized to permit the release of air. Typically, a vent hole may have a maximum width in the range of from about 0.01 mm to about 0.5 mm. An advantage in providing one or more vent holes strategically placed in a membrane rather than use of a membrane with pores large enough to vent air, is that use of the latter is prone to evaporative loss of fluid in the system (a problem also observed with conventional microtiter plates), whereas the former minimizes loss of fluid by evaporation.

In the foregoing descriptions of the device according to the present invention, at least one of the membranes secured to the base is gas permeable; and in a more preferred embodiment, both membranes, secured to their respective surfaces of the base, are gas permeable. In the development of the device according to the present invention, it was found that membranes comprising a polymer membrane having a thickness of in a range of from about 0.002 inches to about 0.004 inches, and treated by ionization, provides an unexpected combination of properties including gas exchange and equilibrium, oxygenation of cells cultured in the device, optical transparency and clarity for observing cells and cell characteristics (e.g., using at least a 60× objective, and more preferably with a 100× objective, of a standard microscope), and an attachment surface and conditions which promote even distribution of anchorage dependent cells (e.g., because of the uniform gas transfer across the membrane used as the attachment surface) as compared to cells contained in wells of a standard microtiter plate. Additionally, with the opening of a microchamber at the top surface of the base and the opening of the microchamber at the bottom surface of the base each being covered by a respective membrane, and with each microchamber comprising a closed, vented environment (and further, since each microchamber is not directly accessed during the liquid handling process), (a) potential cross-contamination between microchambers due to splashing of a fluid is avoided (and also avoided is the variation in assaying associated therewith); and (b) the problems with evaporation encountered with a microtiter plate are avoided or minimized in the device according to the present invention. In a preferred embodiment, the at least one gas permeable membrane of the device according to the present invention has the following gas permeability characteristics with respect to oxygen and carbon dioxide gases: permeability performance at 1 atmosphere and at 37° C. for $O_2$ is in the range of from about 15 to about 40 Barrers, and more preferably about 23 Barrers; and permeability performance at 1 atmosphere and at 37° C. for $CO_2$ is in the range of from about 80 to about 95 Barrers, and more preferably about 88 Barrers. When analyte in the microchamber comprises living cells, such gas permeability characteristics allow a cell respiration more like in vivo growth environments than conventional tissue culture containers or conventional plastic microfluidic card systems. Therefore, the device according to the present invention provides a system more representative of an in vivo environment in assaying an analyte than that provided by a conventional microtiter plate or conventional plastic microfluidic card systems. Preferably, the device comprises membranes that are optically clear and transparent, and more preferably: are transparent in the spectrum range of from about 250 nm to about 900 nm; lack fluorescence under excitation light when the excitation light has a spectrum in the range of from about 260 nm to about 700 nm; and have a sharper diffraction image as compared to the diffraction image of a conventional, plastic tissue culture container (flask or plate or microtiter plate). Regarding the latter, an indelible black ink marker was used to draw a line of about 1 mm in width on both a gas permeable membrane of the device according to the present invention, and the hard plastic surface of a tissue culture container. Using a 20× objective and a standard light microscope, the line observed on the gas permeable membrane remained a well-defined line of about 1 mm. In contrast, a diffuse image of the line was observed on the tissue culture container surface; i.e., the width of the line observed was approximately 3 mm, with the main line being surrounded by dark shadows in which contrast was lost. Thus, the surface of a conventional tissue culture container demonstrated a diffraction image that is at least 100% greater than that observed for a membrane surface of the device according to the present invention.

Also provided is a method according to the present invention for introducing a fluid into the device according to the present invention. For example, fluid may be introduced to the device in the delivery of assay reagent to a microchamber, in delivery of analyte to a microchamber, or in delivery of a combination of assay reagent and analyte to a microchamber. Alternatively, a device according to the present invention may comprise a plurality of microchambers which are pre-filled with analyte. In one embodiment, the method is performed with an automated liquid handling system as known in the art to comprise a programmable pipetting workstation. Typically, such a workstation comprises a multi-pipettor having a plurality of tips. Also typically, the automated liquid handling system aligns the plurality of tips with a plate having a plurality of reaction vessels (e.g., wells), the plate being introduced into the system, such that the plurality of tips can simultaneously dispense a fluid into, or withdraw a fluid from, reaction vessels aligned with the tips. Likewise manual methods for liquid handling also utilize a pipettor (e.g., multi-pipettor) with a plurality of tips.

A method for introducing a fluid into a plurality of microchambers of the device according to the present invention, without directly accessing the microchambers, comprises: (a) aligning a plurality of pipette tips with a plurality of filling ports of the device, wherein each filling port of the plurality of filling ports is in fluid flow communication with a microchamber via a fluid flow groove therebetween; (b) introducing each pipette tip, of a plurality of pipette tips, into the filling port with which it is aligned; (c) dispensing a fluid from each pipette tip according to step (b) wherein the fluid dispensed into each filling port flows through the filling port, along the fluid flow groove, through an opening of the microchamber which is in fluid flow communication with the fluid flow groove, and into the microchamber; and (d) venting air, displaced the fluid flowing in the device (e.g., into the microchamber), by providing airflow communication between the microchamber and a vent aperture. In a preferred embodiment, in the venting step of the method, air is displaced from the microchamber and the air is flowed into the vent aperture. In a more preferred embodiment, the venting further comprises providing one or more vent holes in airflow communication with the vent aperture so that displaced air may flow into the vent aperture and through and out of the one or more vent holes. It will be apparent to one skilled in the art that in the method according to the present invention, a fluid may be introduced into the microchamber at any desired or predetermined fluid level in the microchamber. In assaying an analyte using an optical or spectroscopic analysis, it may be preferable to substantially fill the microchamber (as illustrated in FIG. 9) so that the fluid is in contact with the membrane secured to the top surface of the base (thereby eliminating a meniscus which can distort analysis by imaging techniques).

In one embodiment of introducing a tip of a pipette into a filling port, the tip is inserted through a material selected from the group consisting of a membrane, a septum, and a combination thereof. For example, where a membrane covers the filling port (e.g., the membrane being located at, and secured to, the top surface of the base), each tip can be lowered to contact and puncture the membrane covering the filling port aligned with the tip, in causing the tip to be introduced into the filling port. As illustrated in FIGS. 7 & 8, through the act of puncturing the membrane covering the filling port, membrane flap 65 may be formed around the upper opening of the filling port. Such a membrane flap may serve as a valve means to prevent or minimize a backflow of fluid in the process of removing the tip of the pipette from the filling port. Thus, the punctured membrane comprising the membrane flap may further comprise a valve means. If each filling port further comprises a septum, each tip can be lowered to contact and be inserted into and through the slit of the septum of the filling port aligned with the tip, in causing the tip to be introduced into the filling port. Upon removal of the tip, desirably the septum will reseal. It will be apparent to one skilled in the art from the descriptions herein that the plurality of filling ports may be accessed more than once, in a process of introducing fluid into or withdrawing fluid from the device according to the present invention.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A device comprising:

a base comprising a plurality of apertures, and a top surface and a bottom surface;

two liquid impermeable membranes, wherein one membrane is secured to the top surface of the base and the other membrane is secured to the bottom surface of the base, wherein the membranes are secured to the base in forming a liquid-tight sealing, and wherein at least one of the membranes is gas permeable; and the plurality of apertures comprises one or more sets of apertures, wherein a set of apertures comprises a microchamber with a fluid flow groove, a vent aperture, and a filling port, wherein the microchamber and vent aperture are in airflow communication, and wherein the fluid flow groove comprises fluid flow communication between the microchamber and the filling port of the set in providing for flow of a fluid, when introduced into the filling port, to access the microchamber of the set.

2. The device according to claim 1, wherein both liquid impermeable membranes are gas permeable.

3. The device according to claim 1, wherein the at least one gas-permeable membrane is a single gas permeable membrane secured to the bottom surface of the base.

4. The device according to claim 1, further comprising one or more lids detachably secured to the device.

5. The device according to claim 4, wherein a lid of the one or more lids further comprises a vacuum port.

6. The device according to claim 1, wherein the at least one gas permeable membrane has been treated by ionization.

7. The device according to claim 1, wherein in a set of apertures, a liquid-tight sealing is formed around the filling port, and a liquid tight sealing is formed around the microchamber and the vent aperture.

8. The device according to claim 1, wherein in a set of apertures, a liquid-tight sealing is formed around the filling port and the microchamber with fluid flow groove and the vent aperture.

9. The device according to claim 1, wherein in a set of apertures, a liquid-tight sealing is formed around the filling port and the microchamber with fluid flow groove.

10. The device according to claim 1, wherein the filling port comprises a walled passage comprising a conical shape for receiving a tip of a pipette.

11. The device according to claim 1, wherein the vent aperture extends from the top surface of the base to the bottom surface of the base.

12. The device according to claim 11, wherein the device further comprises a venting channel, wherein the venting channel is in airflow communication with each vent aperture.

13. The device according to claim 1, wherein the vent aperture comprises a single opening formed in the top surface of the base.

14. The device according to claim 1, further comprising a venting system for each set of apertures, wherein the venting system comprises a vent aperture and one or more vent holes formed in the membrane covering the vent aperture.

15. The device according to claim 1, further comprising a venting system for each set of apertures, wherein the venting system comprises a vent aperture, a venting channel, and one or more vent holes, wherein the venting channel provides airflow communication between the vent aperture and the one or more vent holes.

16. The device according to claim 1, wherein the microchamber comprises: an upper opening in the top surface of the base and a lower opening in the bottom surface of the base, wherein the lower opening is in fluid flow communication with the fluid flow groove; and a chamber defined by a sidewall, a portion of the membrane secured to the upper surface of the base which portion covers the upper opening, and a portion of the membrane secured to the lower surface of the base which portion covers the lower opening.

17. The device according to claim 1, wherein the plurality of apertures comprises a plurality of sets of apertures, and wherein the device comprises a number of microchambers ranging from about 24 microchambers to about 144 microchambers.

18. The device according to claim 1, wherein the device further comprises a plurality of septums, each septum being inserted into an aperture.

19. The device according to claim 1, wherein the membranes are of optical transparency and clarity sufficient for permitting the device to be used in an assay having microscopic or spectroscopic analysis.

20. A device comprising:

a base comprising a plurality of sets of apertures, and a top surface and a bottom surface;

two liquid impermeable membranes, wherein one membrane is secured to the top surface of the base and the other membrane is secured to the bottom surface of the base, wherein the membranes are secured to the base in forming a liquid-tight sealing, and wherein at least one of the membranes is gas permeable;

wherein a set of apertures, of the plurality of sets of apertures, comprises a microchamber with a fluid flow groove, a vent aperture, and a filling port, wherein the microchamber and vent aperture are in airflow communication, and wherein the fluid flow groove comprises fluid flow communication between the microchamber and the filling port of the set in providing for flow of a fluid, when introduced into the filling port, to access the microchamber of the set;

wherein the vent aperture comprises one or more openings selected from the group consisting of an opening in the top surface of the base and an opening in the bottom surface of the base, and a single opening in the top surface of the base; and a venting system comprising a vent aperture, and one or more vent holes which allow passage of air therethrough.

21. The device according to claim 20, wherein both liquid impermeable membranes are gas permeable.

22. The device according to claim 20, wherein the at least one gas permeable membrane is a single gas permeable membrane secured to the bottom surface of the base.

23. The device according to claim 20, wherein the device further comprises one or more lids detachably secured thereto.

24. The device according to claim 23, wherein a lid of the one or more lids further comprises a vacuum port.

25. The device according to claim 20, wherein the at least one gas permeable membrane has been treated by ionization.

26. The device according to claim 20, wherein in a set of apertures, a liquid-tight sealing is formed around the filling port, and a liquid tight sealing is formed around the microchamber and the vent aperture.

27. The device according to claim 20, wherein in a set of apertures, a liquid-tight sealing is formed around the filling port and the microchamber with fluid flow groove and the vent aperture.

28. The device according to claim 20, wherein in a set of apertures, a liquid-tight sealing is formed around the filling port and the microchamber with fluid flow groove.

29. The device according to claim 20, wherein the filling port comprises a walled passage comprising a conical shape for receiving a tip of a pipette.

30. The device according to claim 20, wherein the venting system further device comprises a venting channel located between each vent aperture and the one or more vent holes.

31. The device according to claim 20, wherein the microchamber comprises: an upper opening in the top surface of the base and a lower opening in the bottom surface of the base, wherein the lower opening is in fluid flow communication with the fluid flow groove; and a chamber defined by a sidewall, a portion of the membrane secured to the upper surface of the base which portion covers the upper opening, and a portion of the membrane secured to the lower surface of the base which portion covers the lower opening.

32. The device according to claim 20, wherein the device further comprises a plurality of septums, each septum being inserted into an aperture.

33. The device according to claim 20, wherein the membranes are of optical transparency and clarity sufficient for permitting the device to be used in an assay having microscopic or spectroscopic analysis.

* * * * *